(12) United States Patent
Akihiro (10) Patent No.: US 9,211,386 B2
(45) Date of Patent: Dec. 15, 2015

(54) RESPIRATORY TRACT BORE OPENING KEEPING DEVICE

(71) Applicant: Shu-Chen Tsai, New Taipei (TW)

(72) Inventor: Yoshiaki Akihiro, Tokyo (JP)

(73) Assignee: Shu-Chen Tsai, New Taipei (TW)

( * ) Notice: Subject to any disclaimer, the term of this patent is extended or adjusted under 35 U.S.C. 154(b) by 292 days.

(21) Appl. No.: 13/922,265

(22) Filed: Jun. 20, 2013

(65) Prior Publication Data

US 2014/0373849 A1 Dec. 25, 2014

(51) Int. Cl.
*A61M 11/00* (2006.01)
*A61M 16/04* (2006.01)

(52) U.S. Cl.
CPC .................................. *A61M 16/0493* (2014.02)

(58) Field of Classification Search
CPC ............ A61M 16/04; A61M 16/0488; A61M 16/0497; A61M 16/0493
USPC ............. 128/207.14, 207.15, 206.29, 200.26, 128/201.26
See application file for complete search history.

(56) References Cited

U.S. PATENT DOCUMENTS

| | | | | |
|---|---|---|---|---|
| 2,669,988 A * | 2/1954 | Carpenter | | 128/861 |
| 4,305,387 A * | 12/1981 | Reist-Kundig et al. | | 128/202.28 |
| 4,553,540 A * | 11/1985 | Straith | | 128/200.26 |
| 4,640,273 A * | 2/1987 | Greene et al. | | 128/861 |
| 5,003,994 A * | 4/1991 | Cook | | 128/848 |
| 5,365,945 A * | 11/1994 | Halstrom | | 128/848 |
| 5,590,643 A * | 1/1997 | Flam | | 128/200.26 |
| 6,196,224 B1 * | 3/2001 | Alfery | | 128/207.14 |
| 6,325,064 B1 * | 12/2001 | Thornton | | 128/204.18 |
| 7,946,288 B2 * | 5/2011 | Flynn et al. | | 128/200.24 |
| 8,555,886 B2 * | 10/2013 | Colman et al. | | 128/207.14 |
| 8,783,261 B2 * | 7/2014 | Thornton | | 128/848 |

* cited by examiner

*Primary Examiner* — Steven Douglas
(74) *Attorney, Agent, or Firm* — Leong C. Lei (57) ABSTRACT

A respiratory tract bore opening keeping device includes generally a main body that has two sides each connected to a resilient plate. The resilient plates each have a distal end that is remote from the main body and includes a protruding section having an increased thickness formed thereon. The main body has an outer side on which an upper lip positioning section and a lower lip positioning section are formed. The main body has an inner side on which an upper tooth positioning section and a lower tooth positioning section are formed in such a way that the lower tooth positioning section is in front of the upper tooth positioning section. The keeping device is depositeable in the mouth of a person with lips and teeth respectively positioned on the lip and teeth positioning sections to change the configuration of the tongue and the location of the lower jaw.

5 Claims, 9 Drawing Sheets

RESPIRATORY TRACT BORE OPENING KEEPING DEVICE

TECHNICAL FIELD OF THE INVENTION

The present invention generally relates to a keeping device for helping restore respiration and keeping the respiratory tract open, whereby when a person gets unconscious or is affected by other factors to make the brain incapable of controlling muscles, relaxation of respiratory muscles may result, leading to closing of the tracheal tube of respiratory tract and the respiratory tract bore opening keeping device according to the present invention is used with the structure thereof to make physical changes for varying the position of the lower jaw, the mouth floor, and the positions of the left and right lateral parts of the throat so as to make use of the interaction of the relaxed muscle tissues from the oral cavity to the throat to generate a space between the throat and the tongue for conducting air into the respiratory tract and also to apply a force to the mucosal of teeth and lip of the upper jaw of the oral cavity to activate the brain in order to achieve the purposes of smoothening the respiratory tract and helping restore respiration.

DESCRIPTION OF THE PRIOR ART

Various known artificial respirators are currently available and they all aim to open the respiratory tract. However, such artificial respirators are operable by applying a pressure from the outside or use a mechanical device to apply a strong force to the respiratory tissue to open the respiratory tract in order to restore respiration. When the patient has a poor physical condition, such as having only excessively less teeth, cheeks being damaged, or tongue descending to the throat, the treatment process may be hindered.

Thus, a goal of researches of the present inventor and those devoted themselves to the industry is to address the above problems and shortcomings.

SUMMARY OF THE INVENTION

Thus, to overcome the above problems, the present invention provides a plate-like device that is installable simultaneously to lip, cheek mucosal of oral cavity, and periodontium and of which the purposes is to keep the oral cavity and the respiratory tract open by means of the positional coordination among an upper lip positioning section, a lower lip positioning section, an upper tooth positioning section, and a lower tooth positioning section, together with a spring plate that biases an inside surface of the oral cavity outwards, when a user holds the keeping device in mouth.

To achieve the above object, the present invention provides a structure that comprises generally a main body having two sides to each of which a resilient plate is connected. The resilient plates each have a distal end that is remote from the main body and comprises a protruding section having an increased thickness formed thereon. The main body has an outer side on which an upper lip positioning section and a lower lip positioning section are formed. The main body has an inner side on which an upper tooth positioning section and a lower tooth positioning section are formed in such a way that the lower tooth positioning section is in front of the upper tooth positioning section.

The main body has a middle section in which an insertion hole is formed. The insertion hole receives a force application bar to insert therein. An air passage is formed in each side of the insertion hole.

With such a structure, to use, the upper tooth positioning section and the lower tooth positioning section (namely the inner side of the main body) are positioned to face the oral cavity and deposited into the oral cavity. According to the outer configuration of the keeping device, a user may place the upper and lower teeth and upper and lower lips respectively on the upper tooth positioning section, the lower tooth positioning section, the upper lip positioning section, and the lower lip positioning section so as to set the lower jaw more forward that usual and widen the pharyngeal isthmus. The resilient plates bulge the left and right cheeks to prevent the cheeks from collapsing due to factors including lacking of teeth and also to force the palatoglossal arches outwards. The force application bar, when coupled to the insertion hole, enhances the deformation of the tongue to further increase the space of the throat and the air passages help maintain smooth respiration or to conduct out vomits. When the user occludes the keeping device, the oral cavity is constrained by the keeping device to take certain movements and such movements help shorten the time period required for the user to regain conscious and also keep the respiratory tract open until the respiration restores. As such, the advantages and purposes of the present invention can be achieved.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
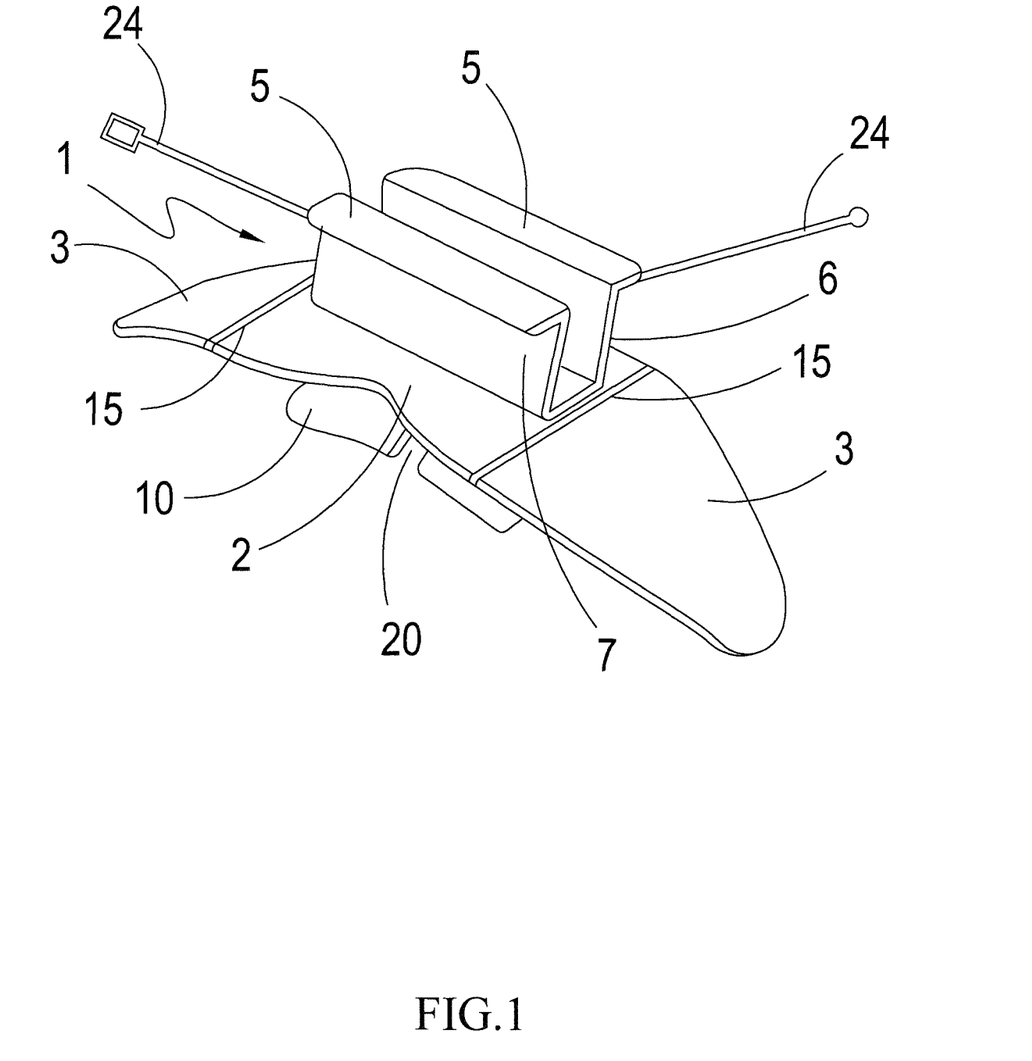
FIG. 1 is a perspective view showing a preferred embodiment of the present invention.
Figure 2:
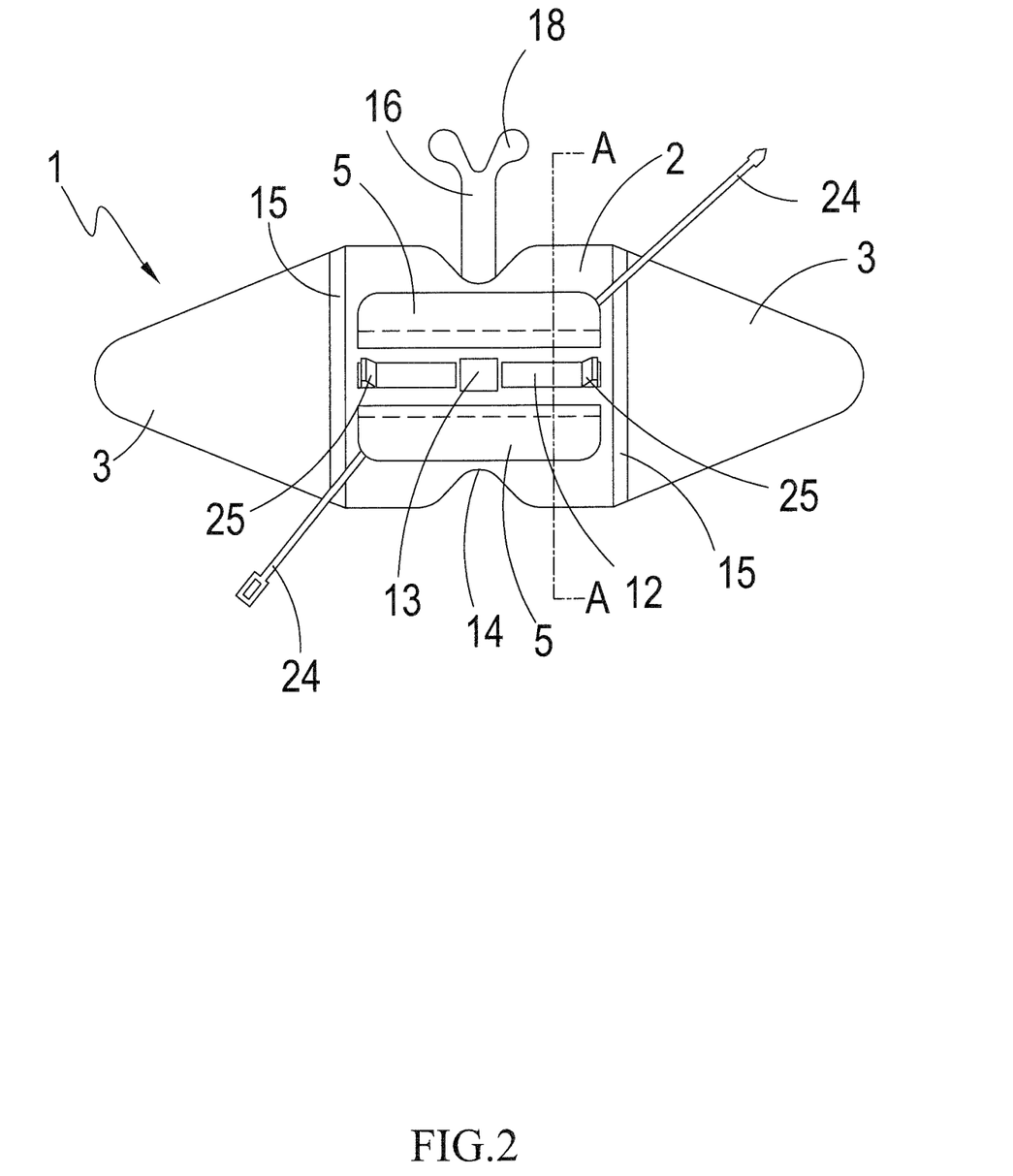
FIG. 2 is a front view of the preferred embodiment of the present invention.

Referring to FIGS. 1, 2, 3, 4, 5, 6, 7, 8, and 9, which are respectively a perspective view, a front view, a rear view, and a top plan view of a preferred embodiment of the present invention, a partial perspective view of the preferred embodiment of the present invention showing an air passage provided with a baffle, a cross-sectional view of the preferred embodiment of the present invention taken along line A-A of FIG. 2, a side elevational view showing a force application bar of the preferred embodiment of the present invention, a front view showing the force application bar of the preferred embodiment of the present invention, and a cross-sectional view showing the force application bar mounted to a main body of the preferred embodiment of the present invention, the structure of the present invention is clearly shown and comprises the following components.

A respiratory tract keeping device 1 comprises a main structure constituted by a main body 2. The main body 2 has two side edges to each of which a resilient plate 3 is connected. The resilient plates 3 each have a distal end that is remote from the main body 2 and comprises a protruding section 19 having an increased thickness formed thereon.

An upper lip positioning section 6 is formed on an outer side of the main body 2.

A lower lip positioning section 7 is formed on the outer side of the main body 2.

Figure 3:
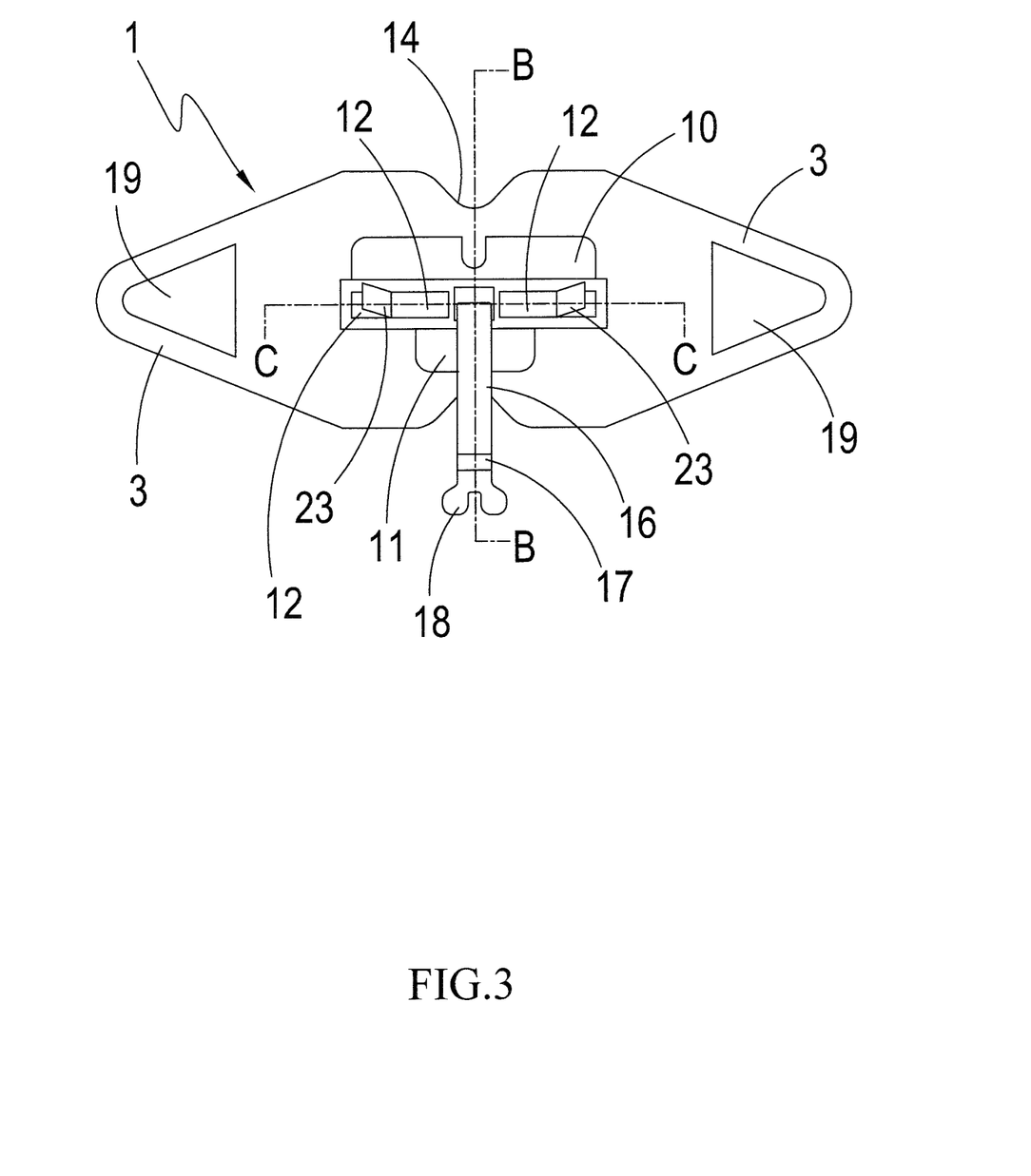
FIG. 3 is a rear view of the preferred embodiment of the present invention.
Figure 4:
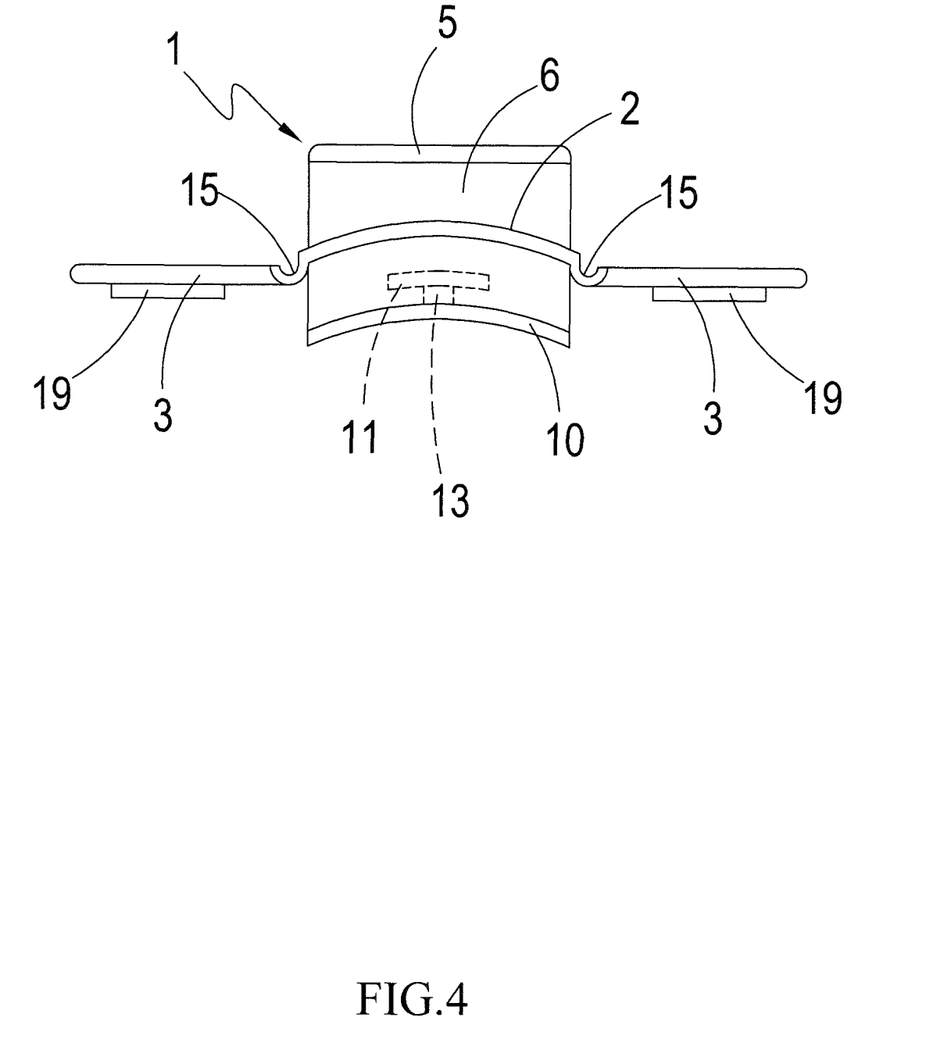
FIG. 4 is a top plan view of the preferred embodiment of the present invention.

An upper tooth positioning section 8 is formed on an inner side of the main body 2.

An lower tooth positioning section 9 is formed on the inner side of the main body 2. The lower tooth positioning section 9 is located in front of the upper tooth positioning section 8.

Figure 9:
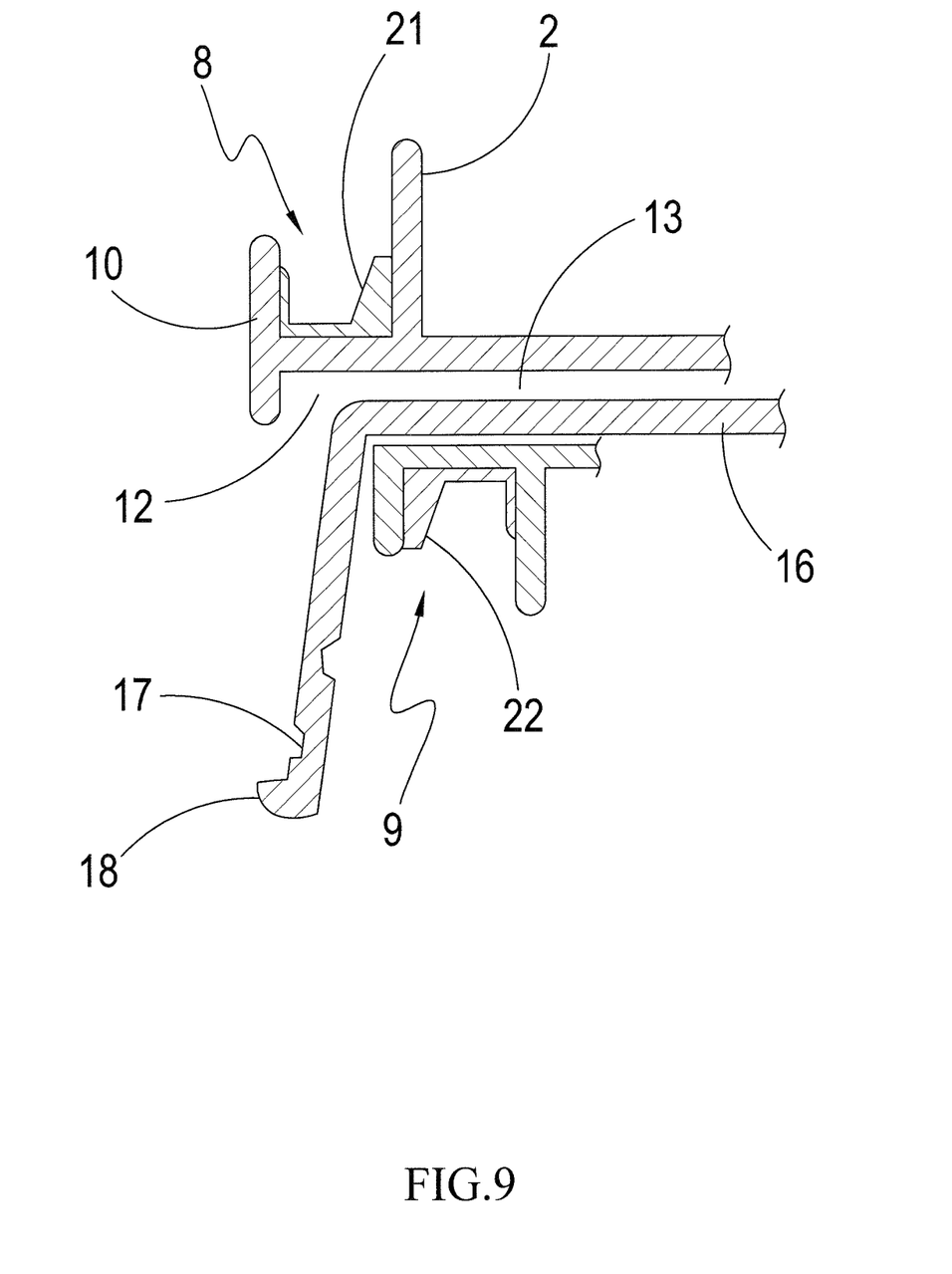
FIG. 9 is a cross-sectional view showing the force application bar mounted to a main body of the preferred embodiment of the present invention.

An insertion hole 13 is formed in a middle section of the main body 2. The insertion hole 13 receives a force application bar 16 to insert therein. An air passage 12 is formed in each side of the insertion hole 13.

Figure 7:
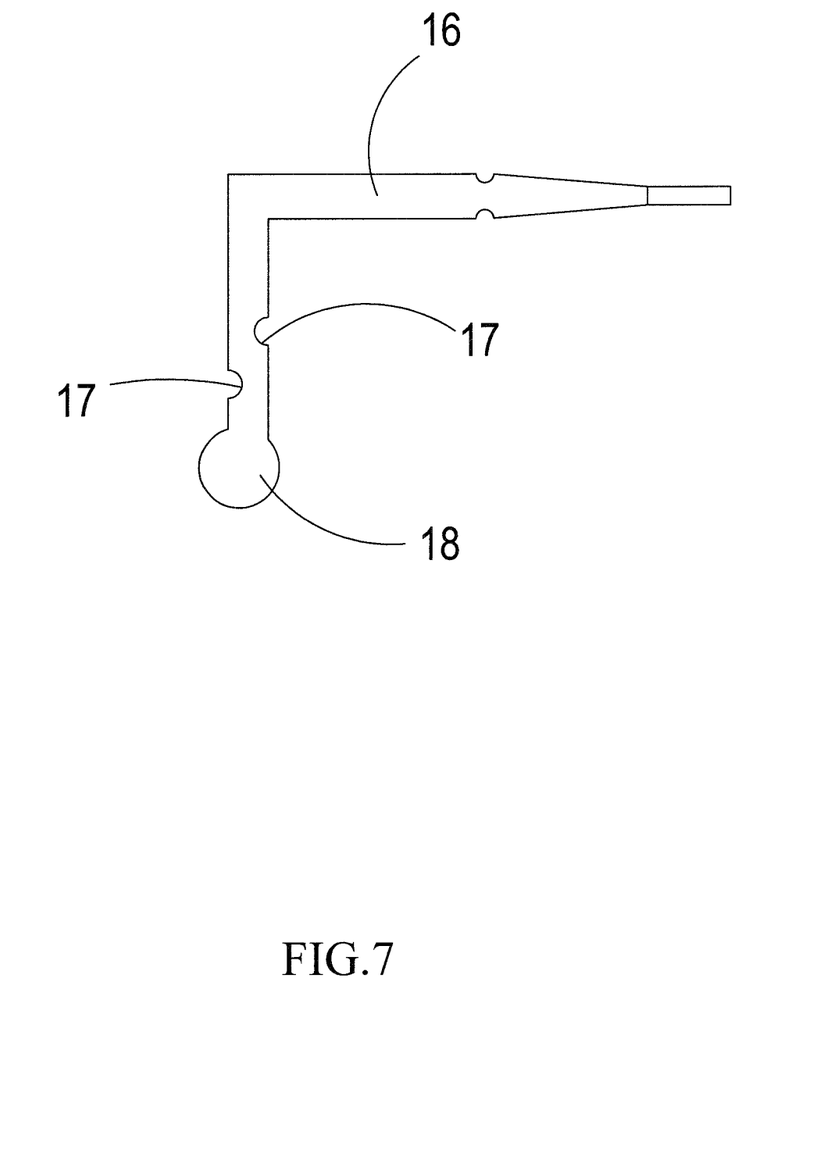
FIG. 7 is a side elevational view showing a force application bar of the preferred embodiment of the present invention.
Figure 8:
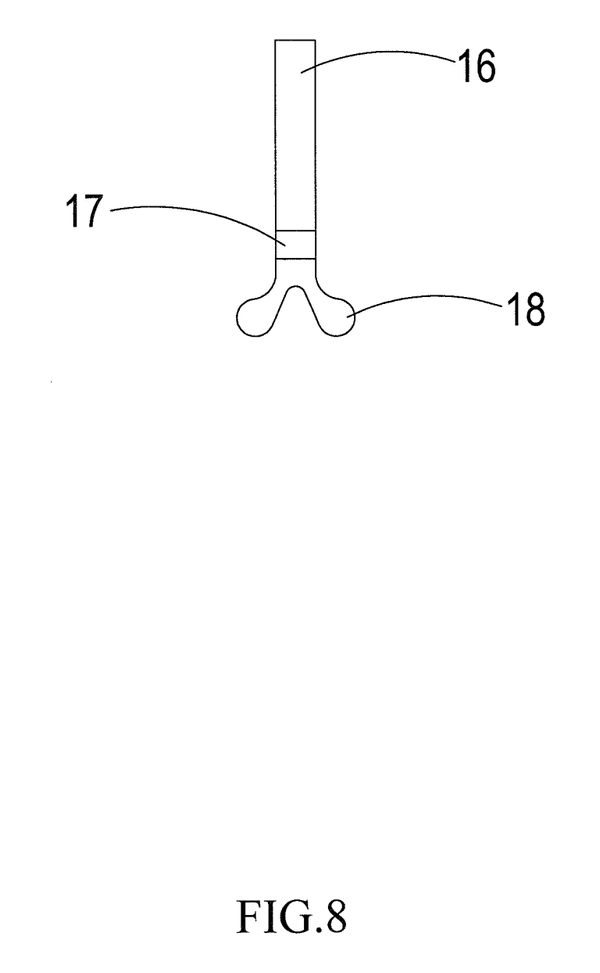
FIG. 8 is a front view showing the force application bar of the preferred embodiment of the present invention.

The force application bar 16 comprises a plurality of notches 17 formed thereon. The force application bar 16 has an end forming an expanded section 18.

The upper tooth positioning section 8 is extended to form an upper erected wall 10, which comprises an upper gum positioning section 21.

The lower tooth positioning section 9 is extended to form a lower erected wall 11, which comprises a lower gum positioning section 22.

The upper lip positioning section 6 and the lower lip positioning section 7 are each extended to form a grip section 5. The grip sections 5 are each connected to a pull string 24.

Figure 6:
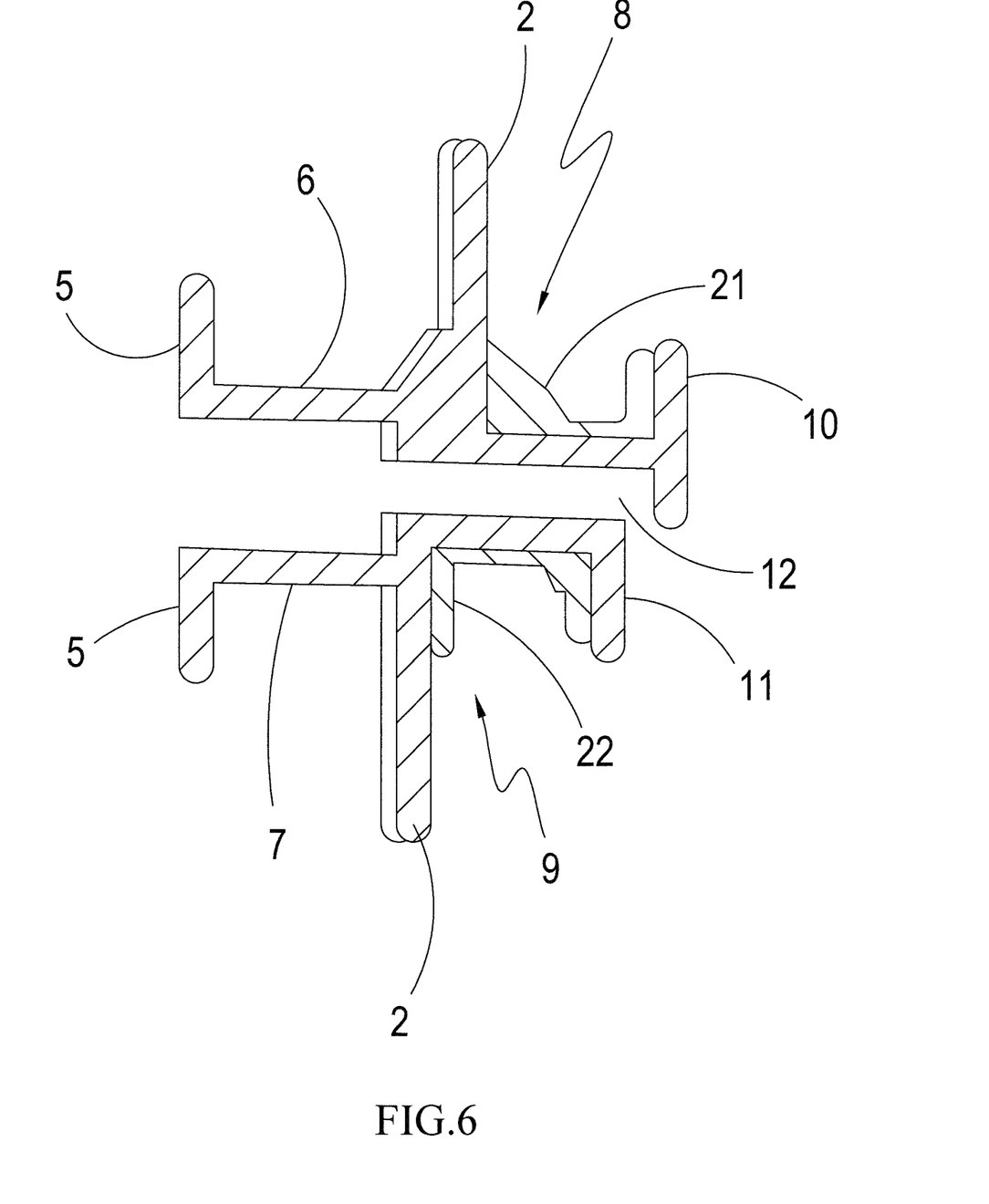
FIG. 6 is a cross-sectional view of the preferred embodiment of the present invention taken along line A-A of FIG. 2.

The main body 2 comprises a curved recess 14 formed in a central portion of each of upper and lower edges. A resilient plate bend section 15 is formed at the connection between the main body 2 and the resilient plate 3. The main body 2 comprises a recess 20 formed in the inside thereof.

Figure 5:
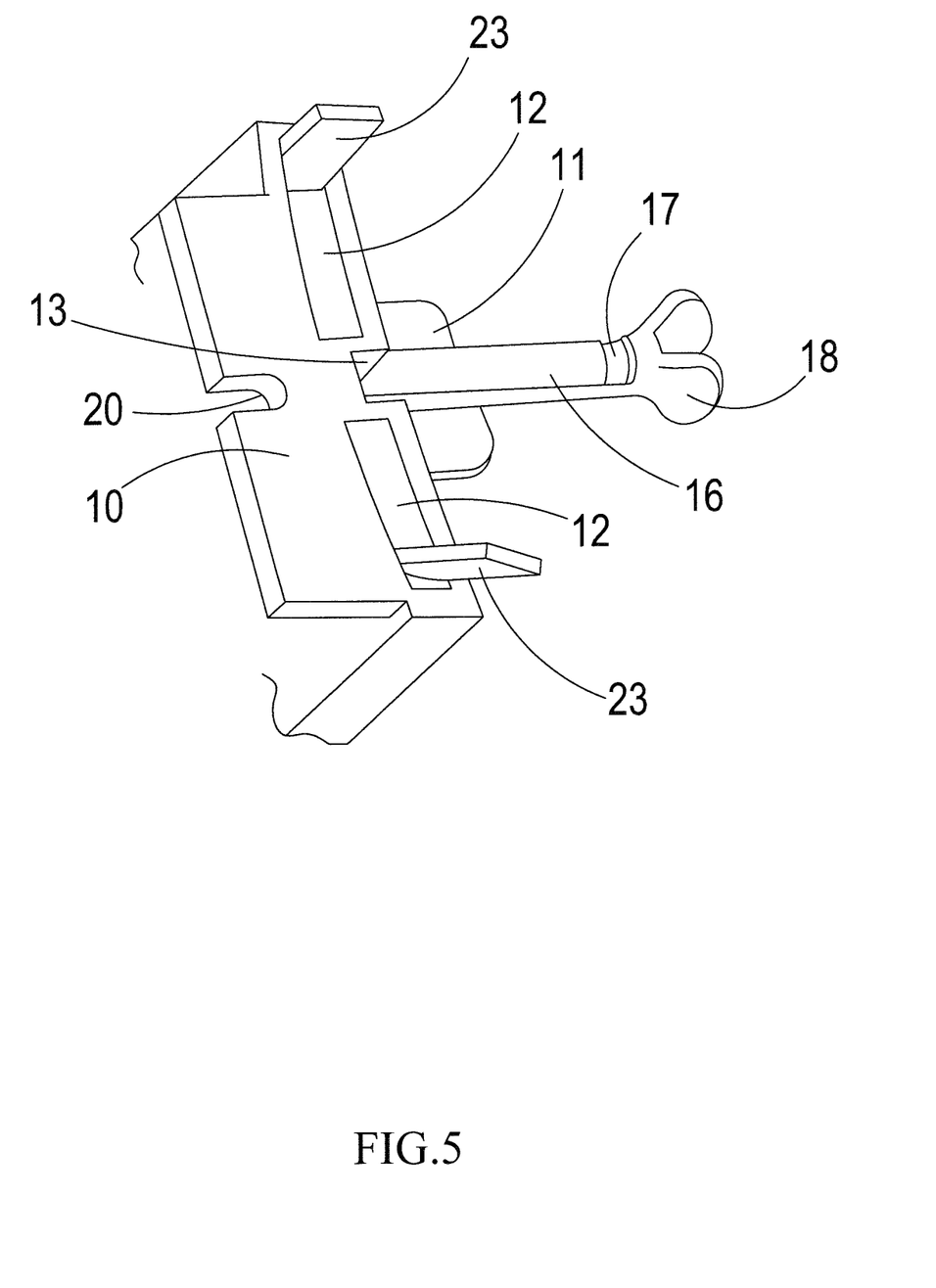
FIG. 5 is a partial perspective view of the preferred embodiment of the present invention showing an air passage provided with a baffle.

The air passages 12 are each provided with a baffle 23 at one side thereof for guiding airflow and an airflow regulation tab 25 for regulation of air flowrate.

With the above described structure, to operate, the upper lip positioning section 6, the lower lip positioning section 7, the upper tooth positioning section 8, and the lower tooth positioning section 9 are used to position and constrain the upper and lower teeth and upper and lower lips of a user and the resilient plates 3 bulge the cheeks to maintain the opening of the respiratory tract. To ensure proper supporting and bulging, the resilient plates 3 are preferably of a surface area that is made as large as possible in order to cover, to a large extent, the inside surfaces of the cheeks. However, an excessively large resilient plate 3 would be of insufficient strength and is difficult to deposit into the mouth. In this respect, the protruding sections 19 function to reinforce and strengthen the resilient plates 3 and also to force the palatoglossal arches outwards to maintain the opening of the respiratory tract. The resilient plate bend sections 15 provide the resilient plates 3 with flexibility in deposition into the oral cavity and the respiratory tract keeping device 1 is allowed to temporarily convert into a three-folded configuration for easy deposition into the oral cavity and to restore the original configuration after being deposited into the oral cavity. The upper tooth positioning section 8 and the lower tooth positioning section 9 are arranged to stagger each other in a front-rear direction so that when the respiratory tract keeping device 1 is occluded, the mandible muscles, the tongue, and the muscle of hyoid bone are forced to move forward thereby opening the pharyngeal isthumus and thus keeping the respiratory tract open. Further, the curved recesses 14 arranged on the main body 2 have a relatively great thickness compared to other portions and may provide stimulation to the portions of the oral cavity between left and right canines to increase the brain blood flow in the right prefrontal lobes for helping shorten the time required for the patient to regain conscious and also for helping restore the function of the respiratory muscles. The force application bar 16 is arranged in such a way that the notches 17 provided thereon help provide the entirety of bar with flexibility and is prevented by means of the expanded section 18 from excessively abrading the tongue to cause the symptoms of pain and nausea. The force application bar 16 presses, from the underside of the tongue, the lingual basis muscles toward the rear, whereby the entire lingual basis, taking a center at the septum lingua, and the portion connecting the tongue diaphragm are pressed rearward to have the back of the tongue showing a recessed configuration and thus opening the respiratory tract. The air passages 12 maintain the respiration of the user and the baffles 23 guide the direction of the airflow and may operate in combination with the airflow regulation tab 25 to regulate the air flow rate, ensuring unobstructed flow or air. Further, besides guiding air flow, the air passages 12 also help conducting out vomits. As such, such a structure provides the advantages and uses of opening the respiratory tract and restoring respiration.

In summary, the technical feature of the respiratory tract bore opening keeping device according to the present invention are as follows:

(1) The upper tooth positioning section 8 and the lower tooth positioning section 9 are arranged in a staggered manner in the front-rear direction to help open the respiratory tract.

(2) The protruding sections 19 help improve the overall strength of the resilient plates 3 to support the inside walls of the cheeks and prevent the cheeks from collapsing and maintain the respiratory tract open.

(3) The curved recesses 14 provide stimulation to oral mucosa to increase the brain blood flow in the right prefrontal lobes for helping shorten the time required for the patient to regain conscious.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A respiratory tract bore opening keeping device, comprising:
   a main body having a first side and a second side;
   two resilient plates, which are respectively connected to two end sides of the main body, the resilient plates each having a distal end remote from the main body and comprising a protruding section having an increased thickness formed thereon;
   an upper lip positioning section, which is formed on the first side of the main body;
   a lower lip positioning section, which is formed on the first side of the main body;
   an upper tooth positioning section, which is formed on the second side of the main body; and
   a lower tooth positioning section, which is formed on the second side of the main body in such a way that the lower tooth positioning section is located in front of the upper tooth positioning section.

2. The respiratory tract bore opening keeping device according to claim 1, wherein the main body comprises a middle section in which an insertion hole is formed, the insertion hole receiving a force application bar to insert therein, an air passage being formed in each side of the insertion hole.

3. The respiratory tract bore opening keeping device according to claim 2, wherein the force application bar comprises a plurality of notches formed thereon, the force application bar having an end forming an expanded section.

4. The respiratory tract bore opening keeping device according to claim 1, wherein the upper tooth positioning section comprises an upper gum positioning section and the lower tooth positioning section comprises a lower gum positioning section.

5. The respiratory tract bore opening keeping device according to claim 1, wherein the upper lip positioning section and the lower lip positioning section each comprises a grip section formed thereon, the grip sections each being connected to a pull string.

\* \* \* \* \*